US008680460B2

(12) United States Patent
Williams et al.

(10) Patent No.: US 8,680,460 B2
(45) Date of Patent: Mar. 25, 2014

(54) CONVERGING-DIVERGING SUPERSONIC SHOCK DISRUPTOR FOR FLUID NEBULIZATION AND DROP FRAGMENTATION

(75) Inventors: Peter T. Williams, Santa Clara, CA (US); Harvey Dean Loucks, Jr., Santa Clara, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 633 days.

(21) Appl. No.: 12/346,089

(22) Filed: Dec. 30, 2008

(65) Prior Publication Data

US 2010/0163719 A1    Jul. 1, 2010

(51) Int. Cl.
*H01J 49/00*    (2006.01)

(52) U.S. Cl.
USPC .......................... 250/281; 250/282; 250/288

(58) Field of Classification Search
USPC ......................................................... 250/281
See application file for complete search history.

(56) References Cited

U.S. PATENT DOCUMENTS

| 2,836,750 | A | * | 5/1958 | Weimer | 96/1 |
| 4,268,460 | A | * | 5/1981 | Boiarski et al. | 261/1 |
| 4,294,208 | A | * | 10/1981 | Wagner | 123/285 |
| 4,909,914 | A | * | 3/1990 | Chiba et al. | 204/164 |
| 5,223,131 | A | * | 6/1993 | Apffel et al. | 210/198.2 |
| 5,513,798 | A | | 5/1996 | Tavor | |
| 6,446,883 | B1 | | 9/2002 | Huang et al. | |
| 6,485,689 | B1 | | 11/2002 | Huang et al. | |
| 6,499,675 | B2 | | 12/2002 | Huang et al. | |

OTHER PUBLICATIONS

Anderson, "Modern Compressible Flow", 2003, pp. 202-211, McGraw Hill.*
Hirabayashi, et al. "Sonic Spray Ionization Method for Atmospheric Pressure Ionization Mass Spectrometry", Analytical Chemistry, Dec. 15, 1994, p. 4557-4559, vol. 66, No. 24.
Hirabayashi, et al. "Sonic Spray Mass Spectrometry", Analytical Chemistry, Sep. 1, 1995, p. 2878-2882, vol. 67, No. 17.
Chapman, "High Speed Flow", 2000, p. 127-131, Cambridge University Press.
Takts, et al. "Electrosonic Spray Ionization", Analytical Chemistry, May 29, 2004, p. 4050-4058, vol. 76, No. 14.
Anderson, "Modern Compressible Flow", 2003, p. 202-211, McGraw Hill.

* cited by examiner

*Primary Examiner* — Phillip A Johnston (57) ABSTRACT

A disruptor apparatus comprises a nozzle comprising: a converging section; a diverging section; and a throat between the converging section and the diverging section. The disruptor apparatus also comprises a holder configured to receive a fluid conduit, which comprises an outlet located in the converging section; and a channel disposed about the holder and configured to guide a gas past the outlet of the fluid conduit, through the converging section, through the throat and into the diverging section where the gas travels at supersonic speed and establishes a standing shock wave in the diverging section. A mass spectrometer and a method are also described.

19 Claims, 6 Drawing Sheets

┌─────────────────────────────────────────────────┐
│ Introducing a Gas into a Converging Section of a Nozzle at │ ~501
│ an Upstream Pressure │
└─────────────────────────────────────────────────┘
                        ↓
┌─────────────────────────────────────────────────┐
│ Subjecting the Diverging Section of the Nozzle to an Ambient │
│ Pressure so that a Ratio of the Ambient Pressure Creates a Standing │ ~502
│ Shock Wave in the Diverging Section │
└─────────────────────────────────────────────────┘
                        ↓
┌─────────────────────────────────────────────────┐
│ In the Converging Section, Mixing a Fluid Comprising an │
│ Analyte with the Gas to Form Drops Directed Towards the │ ~503
│ Standing Shock Wave │
└─────────────────────────────────────────────────┘

FIG. 5

Figure 1:
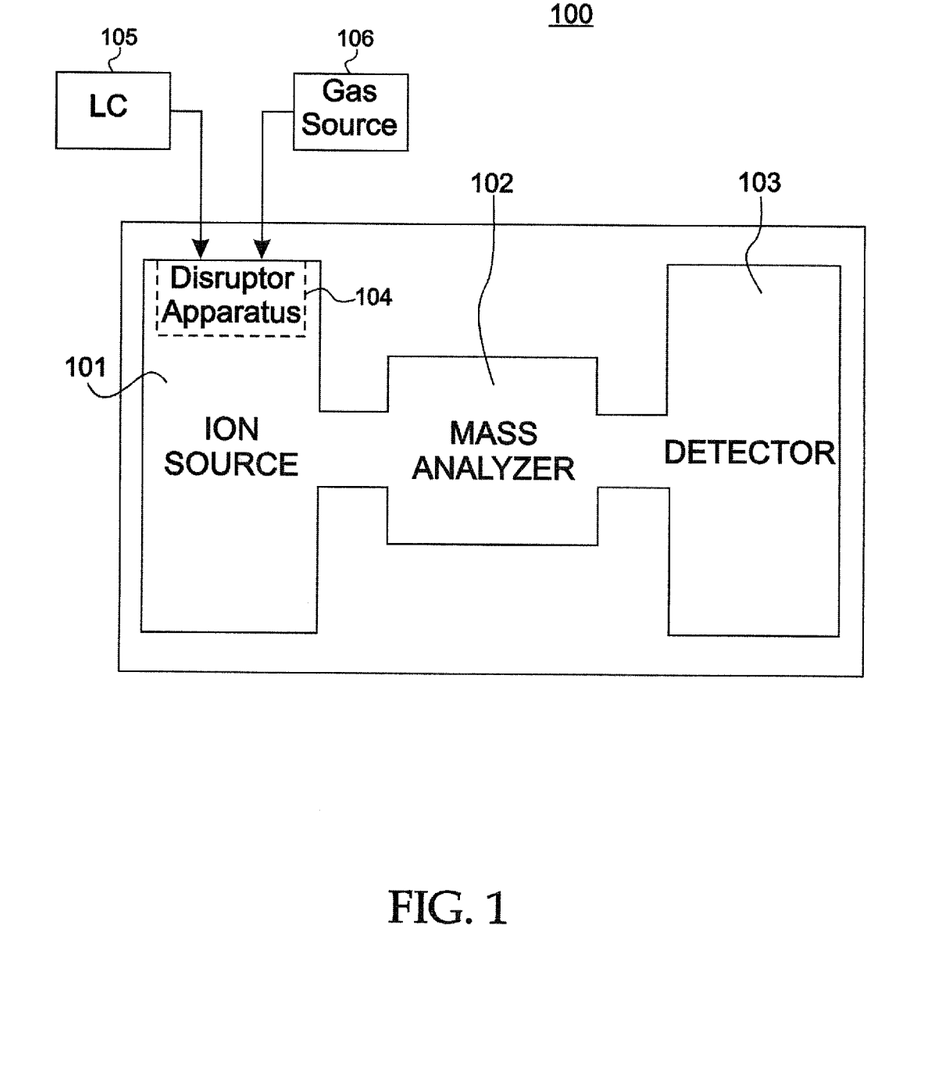
Figure 2A:
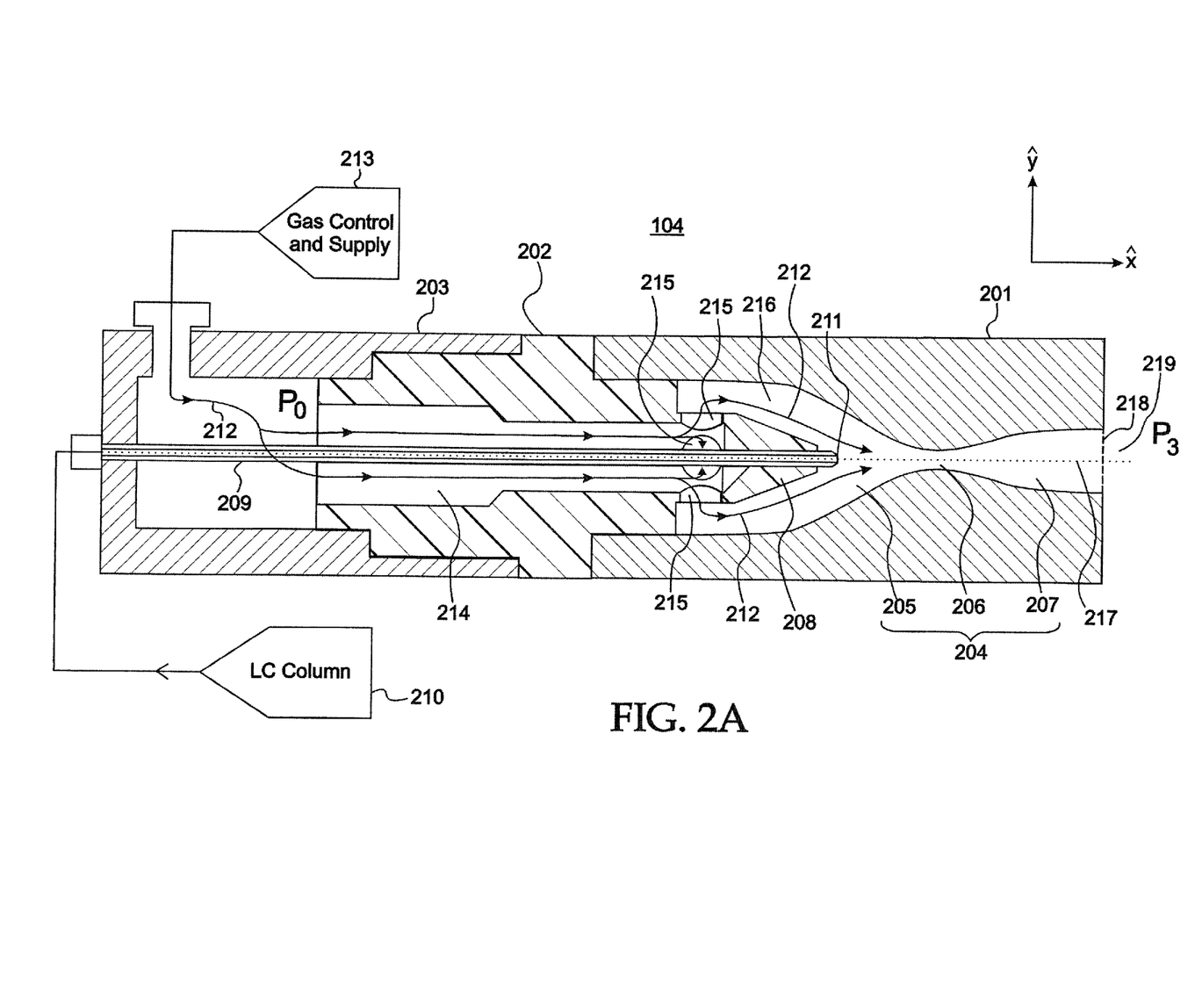

CONVERGING-DIVERGING SUPERSONIC SHOCK DISRUPTOR FOR FLUID NEBULIZATION AND DROP FRAGMENTATION

BACKGROUND

Chemical and biological separations are routinely performed in various industrial and academic settings to determine the presence and/or quantity of individual species in complex sample mixtures. There exist various techniques for performing such separations.

One particularly useful analytical process is chromatography combined with mass spectroscopy, which encompasses a number of methods that are used for separating ions or molecules for analysis. Liquid chromatography ("LC") is a physical method of separation wherein a liquid 'mobile phase' carries a sample containing a mixture of compounds or ions for analysis (analytes) through a separation medium or 'stationary phase.' Fluid from the LC device, which comprises both the analytes and the mobile phase, is provided the analytes to an ion source of a mass spectrometer (MS) for spectroscopic analysis.

Often an electro-spray system is used in the interface between the LC device and a mass spectrometer. In electrospray systems, a voltage is applied to the mobile phase to charge the fluid, and a gas may be provided to assist in nebulizing the fluid. As the fluid comprising the mobile phase and analytes exits a tube or channel annular gas flow around the tube or channel exit forms drops from the fluid. The fluid drops have a charge and, as the mobile phase begins to evaporate, the charge can be transferred to the analytes.

Unfortunately, and among other shortcomings, known drying methods are comparatively low-energy processes and therefore require the drops to travel a significant distance to desolvate. Moreover, repulsion of ions due to known space charge repulsion causes rarefaction. Decreased sample density translates to a comparatively small fraction of the sample ions entering the MS and, hence, reaching a detector in the MS. As such, the efficiency of the MS is reduced.

What is needed, therefore, is a method and apparatus for providing analytes from an LC column to a mass analyzer that overcomes at least the drawbacks of known devices and methods described above.

BRIEF DESCRIPTION OF THE DRAWINGS

The present teachings are best understood from the following detailed description when read with the accompanying drawing figures. The features are not necessarily drawn to scale. Wherever practical, like reference numerals refer to like features.

FIG. 1 is a simplified schematic diagram of a mass spectrometer in accordance with a representative embodiment.

FIG. 2A shows a cross-sectional view of a disruptor apparatus in accordance with a representative embodiment.

FIG. 2B shows a cross-sectional view of part of a first portion of the apparatus shown in FIG. 2A.

FIG. 3 shows a cross-sectional view of an ionizer in accordance with a representative embodiment.

FIG. 4 shows a cross-sectional view of a nozzle provided to a conduit to a mass analyzer in accordance with a representative embodiment.

FIG. 5 shows a flow-chart of a method in accordance with a representative embodiment.

DEFINED TERMINOLOGY

It is to be understood that the terminology used herein is for purposes of describing particular embodiments only, and is not intended to be limiting.

As used in the specification and appended claims, the terms 'a', 'an' and 'the' include both singular and plural referents, unless the context clearly dictates otherwise. Thus, for example, 'a device' includes one device and plural devices.

DETAILED DESCRIPTION

In the following detailed description, for purposes of explanation and not limitation, representative embodiments disclosing specific details are set forth in order to provide a thorough understanding of the present teachings. Descriptions of known systems, devices, materials, methods of operation and methods of manufacture may be omitted so as to avoid obscuring the description of the example embodiments. Nonetheless, systems, devices, materials and methods that are within the purview of one of ordinary skill in the art may be used in accordance with the representative embodiments.

FIG. 1 shows a simplified schematic diagram of a mass spectrometer 100 in accordance with a representative embodiment. The block diagram is drawn in a more general format because the present teachings may be applied to a variety of different types of mass spectrometers. As should be appreciated as the present description continues, devices and methods of representative embodiments may be used in connection with the mass spectrometer 100. As such, the mass spectrometer 100 is useful in garnering a more comprehensive understanding of the functions and applications of the devices and method of the representative embodiments, but is not intended to be limiting of these functions and applications. The mass spectrometer 100 includes an ion source 101, a mass analyzer 102 and a detector 103. The mass spectrometer 100 comprises additional apparatuses, such as electrostatic and RF lenses, as well as other apparatuses not shown. Such apparatuses are known and are not described in detail to avoid obscuring the description of representative embodiments.

The ion source 101 comprises a disruptor apparatus 104. The disruptor apparatus 104 is configured to receive fluid from an LC device 105 and inert gas from a gas source 106 and functions as an interface between the LC device 105 and the mass spectrometer 100. As described in more detail below, the disruptor apparatus 104 nebulizes the fluid from the LC device 105 to generate drops and then fragments the drops to form droplets (not shown in FIG. 1). The droplets are desolvated leaving analyte ions and gas molecules. The resulting analyte ions (not shown in FIG. 1) are provided to mass analyzer 102. The mass analyzer 102 may include a conduit such as a sleeve, transport device, dispenser, capillary, nozzle, hose, pipe, pipette, port, connector, tube, orifice, orifice in a wall, coupling, container, housing, structure or other apparatus used to transport analyte ions from the ion source 101 to the detector 103. The mass analyzer 102 may be one of a number of known devices used to filter ions based on a charge-to-mass ratio. Illustratively, the mass analyzer comprises one of a quadrupole mass analyzer, an ion trap, a tune-of-flight device, among others. The detector 103 may be a known ion detector used to detect the analyte ions that are collected and separated by the mass analyzer 102 according to their mass-to-charge ratio. The detector 103 typically also includes known hardware, software or firmware, or a combination thereof useful in detecting analytes.

FIG. 2A shows a cross-sectional view of disruptor apparatus 104 in accordance with a representative embodiment. The disruptor apparatus 104 comprises a first portion 201, a second portion 202 and a third portion 203. The first portion 201 defines a nozzle 204 that extends axially through the first portion. The nozzle 204 comprises a converging section 205, a throat 206 and a diverging section 207 in order, in tandem. The second portion 202 comprises a holder 208, and the first portion 201 is configured to receive a part of the holder 208 remote from the throat 206 and diverging section 207. The holder 208 maintains an outlet 211 of a fluid conduit 209 in a position to facilitate nebulization. The fluid conduit 209 is connected at one end to an output of an LC column 210 and provides fluid at the outlet 211 for nebulization as described more fully below.

In the embodiment shown in FIG. 2A, the holder 208 maintains the fluid conduit 209 in a position such that the outlet 211 is located in the first portion 201 at a position in the converging section 205 of the nozzle 204 to facilitate nebulization. In an alternative embodiment, the fluid conduit 209 could be extended through the throat 206 so that the outlet 211 is located in the diverging section 207 of the nozzle 204.

The third portion 203 is coupled to the second portion 202. In the example shown, a part of the third portion 203 accommodates a part of the second portion 202. The third portion 203 receives a gas 212 from a gas control and supply 213. Typically, the gas 212 is an inert gas such as nitrogen. The LC column 210 is connected to the fluid conduit 209 via a connection in the third portion 203, and as described provides LC fluid (not shown in FIG. 2A) to the fluid conduit 209 there through.

The second portion 202 comprises an axial gas conduit 214 disposed about the fluid conduit 209, and comprises orifices 215 that extend radially from the axial gas conduit 214 to a channel 216, which is illustratively formed by and between the first portion 201 and the second portion 202. The axial gas conduit 214 is configured to direct the gas 212 toward the orifices 215. The orifices 215 are configured to direct the gas 212 into the channel 216 of the first portion 201 where the gas 212 propels drops (not shown in FIG. 2A) of fluid resulting from nebulization of the fluid provided at the outlet 211. As described more fully herein, the drops are propelled by the gas 212 through the converging section 205 and the throat 206, and into the diverging section 207. The drops are then propelled by the gas 212 into a standing shock wave 218 established by the flow of gas 212 through nozzle 204.

The fluid provided at the outlet 211 of the fluid conduit 209 is nebulized by known methods. Notably, in representative embodiment, the fluid provided at the outlet 211 is nebulized by known electrospray methods; or by gas-assisted nebulization, by or electrospray with gas-assisted nebulization. The gas 212 may be used to effect gas-assisted nebulization, or in electrospray with gas-assisted nebulization. If electrospray is used as the sole method of nebulization, the gas 212 would not be used in the nebulization of the fluid to form drops, but only to propel the drops through the nozzle 204 and into the standing shock wave 218.

In a representative embodiment, the orifices 215 are arranged at 90° intervals about a longitudinal axis 217 through the disruptor apparatus 104. In another representative embodiment, the orifices 215 are arranged at 120° intervals about the longitudinal axis 217. In still other representative embodiments there are more than four orifices, while in other embodiments there are three or fewer orifices. The regular spacing of the intervals is merely illustrative, and irregular spacing of the orifices 215 is contemplated.

In representative embodiments, the material used for the first portion 201 and the fluid conduit 209 is electrically conducting, while the material used in the second portion 202 is electrically insulating. The third portion 203 may be either electrically conducting or insulating. Illustratively, the electrically conducting material comprises one or more of a metal, a metal alloy, an electrically conducting composite material, or a coated plastic material. Similarly, the insulating material is illustratively a polymer (e.g., plastic), a composite material or other suitable electrical insulator. As will become clearer as the present description continues, the conducting and insulating materials are selected to facilitate establishing an electrical potential difference between the first portion 201 and the fluid conduit 209.

In accordance with a representative embodiment, in operation, the disruptor apparatus 104 first nebulizes fluid from the LC column 210 by electrospray with gas-assisted nebulization of fluid provided at the outlet 211 disposed in the converging section 205, and by passing the gas 212 past the outlet 211. Alternatively, the nebulization occurs solely by gas assisted nebulization of fluid at the outlet 211 by passing the gas 212 past the outlet 211. Next, the drops (not shown in FIG. 2A) formed by the nebulization are propelled by the gas 212 through the throat 206 and into the diverging section 207. As described more fully herein, the drops attain a substantially greater velocity than the velocity attained by known nebulization methods, and impact on a standing shock wave 218 located in the diverging section or at or near an exit 219 of the diverging section 207. The impact of the drops with the standing shock wave 218 fragments the drops into droplets (not shown in FIG. 2A) by imparting at least three (3) orders of magnitude and as much as approximately four (4) orders of magnitude more energy into the drops than known practice gas assisted nebulization.

The gas 212 is provided at an upstream pressure $P_0$ that is chosen to establish the standing shock wave 218. As described more fully herein, the Mach number of the standing shock wave 218, which refers to the standing shock wave caused by gas 212 having a velocity of the same Mach number upon entering the standing shock wave 218, is dependent upon the ratio of the upstream pressure ($P_0$) to the ambient pressure ratio ($P_3$) at the outlet of the diverging section 205. In representative embodiments, the ratio $P_0/P_3$ is selected to be on the order of approximately 4.0 or higher to attain a desired Mach number to ensure suitable fragmentation of drops of nebulized fluid. It is noted that the upstream pressure $P_0$ is more readily controlled than the ambient pressure $P_3$, which is, for example, the pressure of a chamber of the ion source 101 and is normally atmospheric pressure.

In accordance with representative embodiments, the disruptor apparatus 104 significantly desolvates or substantially completely desolvates the mobile phase of the LC fluid leaving analyte ions. Among other benefits, the disruptor apparatus 104 produces a comparatively high density cloud of analyte ions near the entrance of the mass analyzer 102. By contrast, and as alluded to above, because of the time and distance required to desolvate the fluid drops formed by known low energy drop formation, current nebulizers produce a low-density cloud of analyte ions. As such, using known nebulizers, the nebulizer outlet must be placed comparatively far from the inlet to the mass analyzer. The extra time and distance resulting from this separation allow space charge forces to cause the analyte ions to move apart and become less dense. Therefore, by known methods and apparatuses fewer analyte ions are provided to the mass analyzer 102.

In certain embodiments such as described below in connection with connection FIG. 3, the disruptor apparatus 104 is a component of the ion source 101. In other embodiments such as described below in connection with FIG. 4, the disruptor apparatus 104 functions as the ion source 101 and is coupled directly to a conduit to a mass analyzer 102. Thus, whether the disruptor apparatus 104 is a component of the ion source 101 or functions as the ion source 101 of the mass spectrometer 100, the disruptor apparatus 104 comprises an interface between the LC column and the mass spectrometer.

Figure 2B:
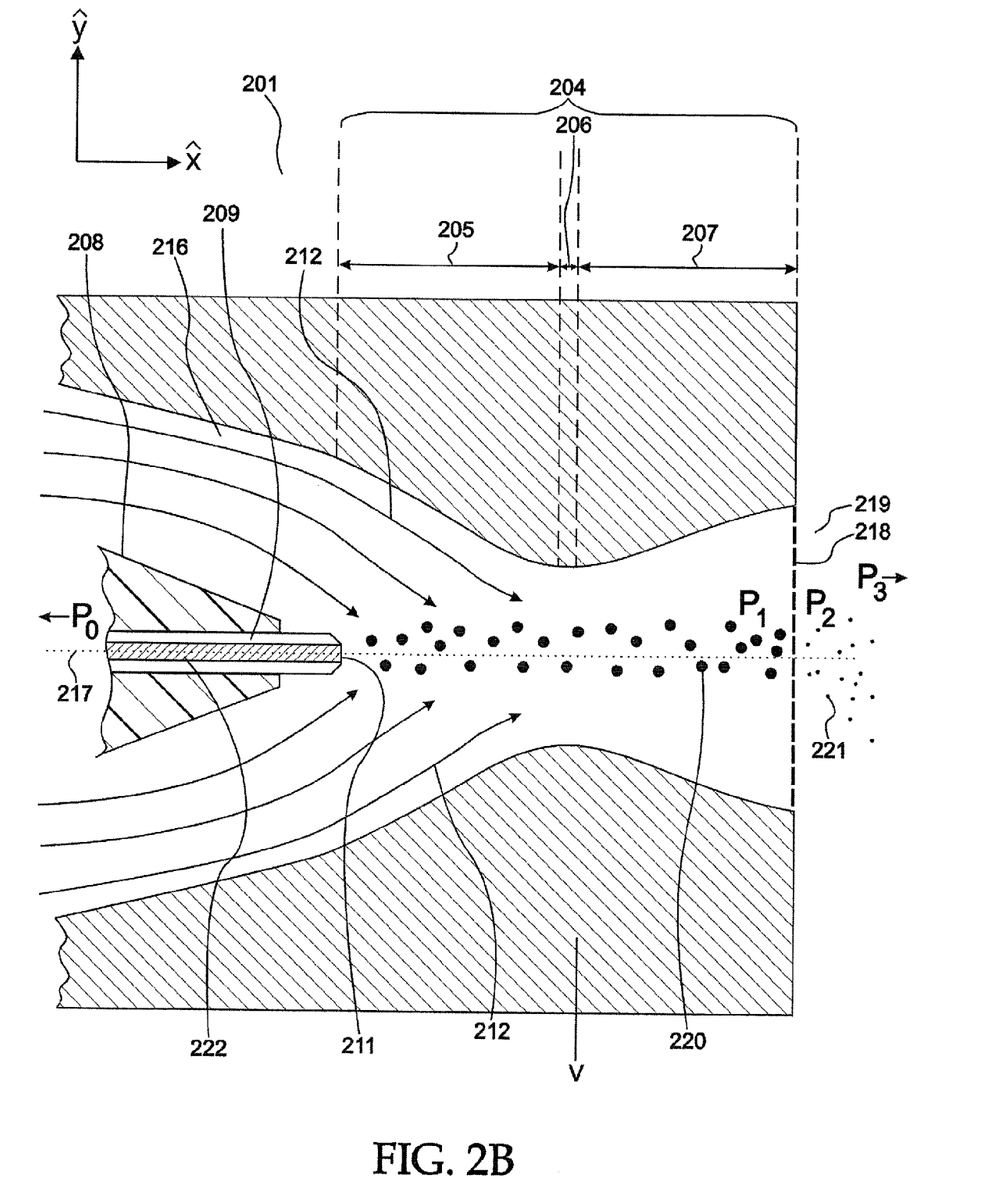

FIG. 2B is a cross-sectional view showing a part of the first portion 201 of the disruptor apparatus 104, which is shown in an enlarged view to facilitate the description of the nozzle 204. As shown, the throat 206 is situated between the converging section 205 and the diverging section 207; and the throat 206 is a part of nozzle 204 in which the cross-sectional area of the nozzle 204 in the x-z plane orthogonal to the longitudinal axis 217 is a minimum. Notably, the dashed lines delineating the boundaries of the converging section 205, the throat 206 and the diverging section 207 are set in approximate position. Generally, the converging section 205, as its name implies, is a section where the cross-sectional area of the nozzle 204 in the x-z plane orthogonal to the longitudinal axis 217 decreases with respect to the axial position (+x-direction) towards the throat. The diverging section 207 is a section where the cross-sectional area of the nozzle in the x-z plane orthogonal to the longitudinal axis 217 increases with axial position (+x direction) away from the throat 206. Moreover, while the throat 206 comprises a region of the nozzle 204, it is a point at which the cross-sectional area of the nozzle 204 is a minimum.

As noted above, the holder 208 maintains the outlet 211 of the fluid conduit 209 at a location in the first portion 201 at a position in the converging section 205 of the nozzle 204 to facilitate nebulization. Fluid 222 from the LC column 210 flows through the fluid conduit 209 and the gas 212 converges about the outlet 211 as it traverses the converging section 205. The gas 212 converging near the outlet 211 assists in nebulizing the fluid 222 at the outlet 211 via shear forces to generate drops 220.

The gas 212 propels the drops 220 through the converging section 205, through the throat 206 and into the diverging section 207. The ratio of the upstream pressure to ambient pressure ($P_0/P_3$), dimensions of the converging section 205, the throat 206, and diverging section 207 of the nozzle 204 of disruptor apparatus 104 are selected so that the gas 212 flowing through the nozzle 204 creates a standing shock wave 218 at a selected location within the nozzle 204. In certain embodiments, the standing shock wave is positioned at the exit 219 of the diverging section 207. In other embodiments, the standing shock wave 218 is positioned within the diverging section 207, but comparatively close to the exit 219 of the diverging section 207. As described more fully below, the positioning of the standing shock wave 218 away from the throat 206 affords sufficient distance for the drops 220 to be accelerated by the gas 212 and thereby attain a comparatively high velocity before the drops 220 impact the standing shock wave 218. By similar analysis, standing shock wave 218 should not be located in proximity to the throat 206 because the drops 220 will not have sufficient distance to attain a sufficient velocity for acceptable fragmentation of the drops 220 to occur. As such, the pressure ratio ($P_0/P_3$) and dimensions of the components of the nozzle 204 are selected to avoid locating the standing shock wave 218 in proximity to the throat 206.

The gas 212 attains a velocity of at least approximately Mach 1.2 in the diverging section 207. In certain embodiments, the gas 212 attains a velocity of at least approximately Mach 3.0 in the diverging section 207; and in certain embodiments, the gas 212 attains a velocity of at least approximately Mach 4.0. The comparatively high velocity of the gas 212 serves to propel the drops 220 through the diverging section 207 at comparatively high velocity as well. As they traverse the diverging section 207, the drops 220 can attain a velocity nearing that of the gas 212. The velocity of the drops 220 relative to the gas 212 depends on the distance between the throat 206 and the standing shock wave 218. In representative embodiments, by providing a diverging section 207 of suitable length, drop velocities of 80% relative to the gas velocity are readily attainable. The drops 220 attain their maximum velocity in the diverging section 207 and impact the standing shock wave 218 at substantially normal incidence. The combination of the comparatively high speed attained by the drops 220 and their substantially normal incidence to the standing shock wave 218 fosters efficient fragmentation of the drops 220.

The normal incidence of the drops 220 to the standing shock wave 218 is more disruptive than a network of weak oblique shocks as provided in certain known nebulizers. As the drops 220 enter the standing shock wave 218, the standing shock wave 218 will flatten the drops 220; deposit a comparatively large vortex ring around the periphery of the drops 220; and create a comparatively large instantaneous difference between the drop speed and the ambient gas speed, generating shear, which will cause the drops 220 to fission. Drops 220 fragment into droplets 221, and after emerging from the standing shock wave 218, the droplets 221 enter a region at an ambient pressure $P_3$, and the velocity of the droplets 221 reduces very rapidly to ambient gas velocities. This rapid change in velocity imparts energy to the droplets 221 in the form of heat. Accordingly, in a representative embodiment, as the fluid 222 from the LC column 210 travels through the disruptor apparatus 104, it undergoes a gas-assisted nebulization upon mixing with the gas 212 in the converging section 205; and a high-energy fragmentation caused by accelerating the drops 220 along a direction normal to and through the highly energetic shock wave 218. By way of comparison, the energy imparted to the drops 220 by the disruptor apparatus 104 is on the order of $10^3$ to $10^4$ greater than the energy imparted by known nebulizer apparatuses and methods for similar upstream and ambient pressures, and inert gas flow rates of inert gas. Illustratively, the energy imparted to the drops 220 with the velocity of gas 212 in the diverging section 207 of approximately Mach 3.0 or greater is sufficient to substantially completely desolvate the droplets 221.

As noted previously, the fluid conduit 209 and the first portion 201 are electrically conductive and the holder 208 is electrically insulating. The insulator allows an optional voltage (designated V in FIG. 2B) to be maintained between the fluid conduit 209 and the first portion 201 that there exists an electrical potential gradient that charges the drop 220 as they exit the fluid conduit 209. In a representative embodiment, the fluid conduit 209 is maintained at a ground potential and a positive voltage is applied to the first portion. The present teachings contemplate foregoing the establishing of a voltage as just described. Rather, aiding in the imparting of electric charge to drop 220 by the application of an electric field at the outlet 211 may be unnecessary as droplets 221 resulting from the fissioning may comprise charged analyte ions after passing through the standing shock wave 218.

Thus, in accordance with a representative embodiment, the disruptor apparatus 104 provides smaller droplets as droplets 221. The droplets 221 require a comparatively shorter desolvation time in a drying stage of the ion source. A reduced desolvation time beneficially results in a higher density analyte ion cloud near the inlet to the mass analyzer 102. Ultimately, this higher analyte ion density produces a greater ion current into the mass analyzer 102, which in turn leads to higher sensitivity and lower detection levels.

Referring to FIGS. 2A and 2B, and as alluded to above, in the converging/diverging nozzle of disruptor apparatus 104, the ratio of pressures, $P_0/P_3$ and the dimensions of the exit 219 of diverging section 207 and the throat 206 of the nozzle 204 dictate the conditions for both supersonic flow of gas 212 and the location of the standing shock wave 218. In accordance with representative embodiments, the gas 212 traveling through the nozzle 204 of the disruptor apparatus 104 can readily attain a velocity in the diverging section 207 of at least M=1.2 and more typically in the range of approximately M=3 to approximately M=4. By way of quantitative example, a minimum pressure ratio of $P_0/P_3$ that must be exceeded to achieve supersonic speeds is 1.89 where the gas 212 is air or, likewise, nitrogen. As such, with the a pressure ratio $P_0/P_3$ of approximately 2 or greater, the gas 212 can attain supersonic speeds in the diverging section 207, the standing shock wave 218 can be established, and the fragmentation of drops 220 into droplets 221 can be achieved.

As noted above, the cross-sectional area of the exit 219 of the diverging section 207 and the cross-sectional area of the throat 206 impact the position of the standing shock wave 218. A given specified upstream pressure $P_0$ and downstream post-shock pressure $P_3$ determine the ratio of the area of the exit 219 of the diverging section 207 to the area of the throat 206 that ensures that the standing shock wave 218 exists and is situated at the exit 219 of the diverging section 207. By creating the nozzle 204 with this area ratio, or substantially with this area ratio, a standing shock wave 218 substantially normal to the longitudinal axis 217 is formed at the exit 219. For example, selecting ambient pressure $P_0$ to be approximately 4 atm, which can be readily achieved, a design Mach number is required so that the pre-shock wave static pressure $P_1$ begets the post-shock pressure $P_2$ that is substantially equal to the ambient pressure $P_3$, which is illustratively 1 atm.

Many details of attaining supersonic gas flow in a convergent/divergent nozzle and the positioning of a standing shock wave are known. Such details, can found, for example, in Section 7.2 of C. J. Chapman, "High Speed Flow", Cambridge University Press (2000), ISBN 0-521-66647-3. The disclosure of this section of this text is specifically incorporated herein by reference.

Figure 3:
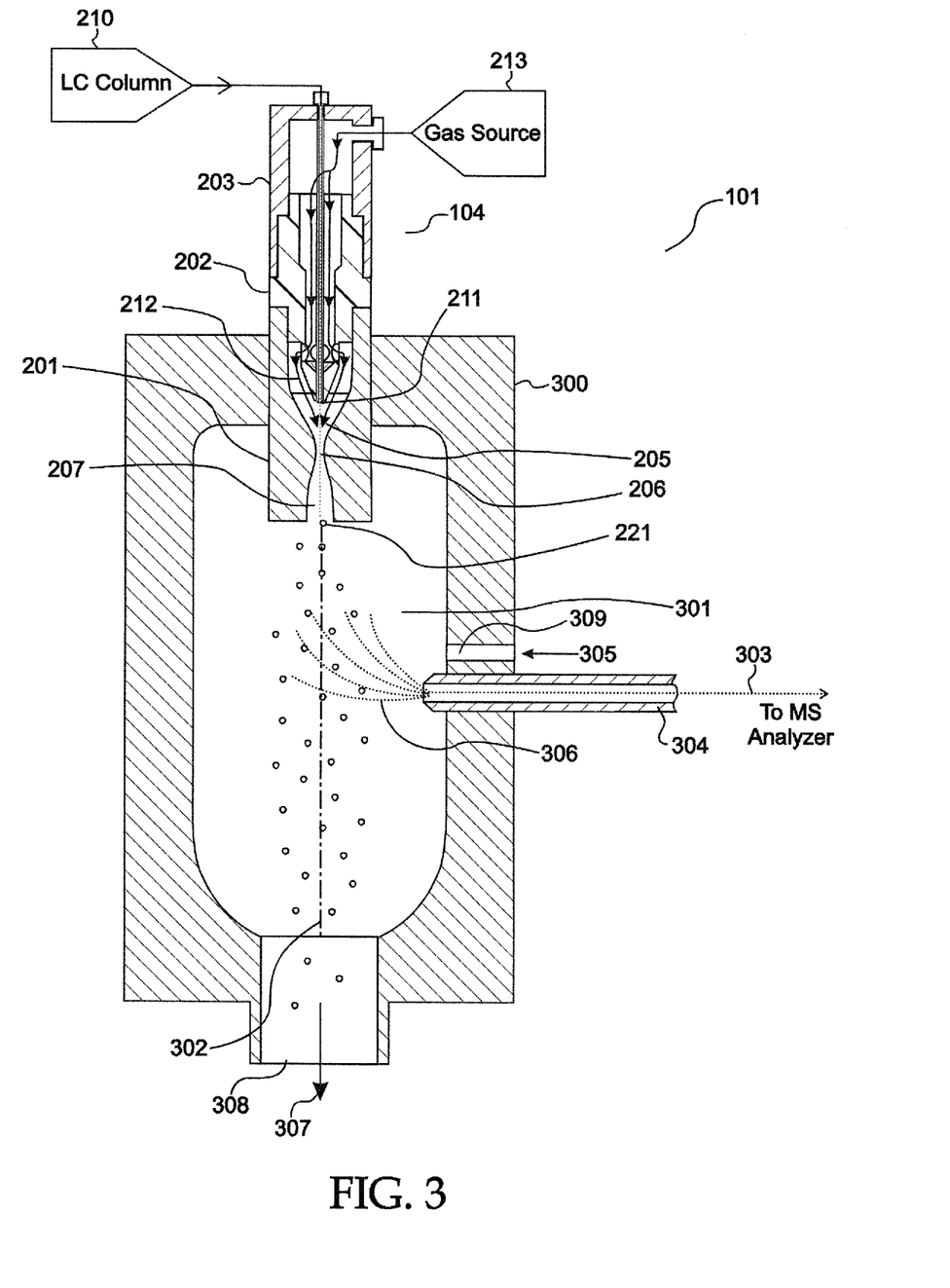

In known methods of nebulization used in many LC applications, the predominant mechanism causing drop fissioning is not kinetic energy (KE) deposition resulting from the interaction of the drops with a standing shock wave according to the representative embodiments described above, but rather electrostatic repulsion/fissioning of drops as the mobile phase evaporates. In known apparatuses and systems, space charge, which is a term used to describe mutual electrostatic repulsion of analyte particles and drops, limits maximum transmission not to a fraction of the total number of analyte particles, but to a maximum absolute quantity. That is, the space charge limit is reached for ions in a particular device, attempts to increase analyte throughput does not help. In contrast, during the comparatively rapid fragmentation of drops 220 into droplets 221, the droplets 221 acquire a static electric charge due to non-uniform distribution of charge in the original drop as well as the splitting of polarized molecules. Moreover, one way to mitigate space charge quenching of analyte current is to decrease the residency time ions spend in desolvation. Therefore, by desolvating the droplets 221 more rapidly and providing the ions into the mass analyzer more quickly, the maximum current (in absolute value) is increased. In embodiments described herein, because the droplets 221 are comparatively small, a comparatively greater area-to-volume ratio is attained and the speed of desolvation is increased compared to known methods and apparatuses. As described below, the nozzle of disruptor apparatus 104 beneficially improves the speed of desolvation, increasing the space-charge-limited current and allowing more analytes to be passed into the mass spectrometer device. These and other beneficial aspects of the apparatus are described presently in connection with representative embodiments shown in FIGS. 3 and 4.

FIG. 3 is a cross-sectional view of ion source 101 in accordance with a representative embodiment. The ion source 101 comprises a housing 300 and the disruptor apparatus 104, which extends through the housing 300 into a chamber 301 bounded by the housing 300. Droplets 221 emerge from the diverging section 207 of the nozzle 204 of disruptor apparatus 104 and enter the chamber 301. In a representative embodiment, the diverging section 207 is oriented along a longitudinal axis 302 that is substantially orthogonal to a conduit longitudinal axis 303 of a conduit 304. While the orthogonal arrangement may be used, it is not essential. A variety of angles (obtuse and acute) may be defined between the longitudinal axis 302 and the conduit longitudinal axis 303 of the conduit 304. Alternatively, the longitudinal axis 302 may be aligned with the conduit longitudinal axis 303 of the conduit 304. Illustratively, the pressure in the chamber 301 is maintained at about 20 Torr to about 2000 Torr. Operation at atmospheric pressure (around 760 Torr) and non-atmospheric pressure is thus possible.

The mass analyzer 102 includes the conduit 304 or any number of capillaries, conduits or devices for receiving and moving the analyte ions from the chamber 301 to the detector 103. The conduit 304 extends into the housing 300 downstream from the disruptor apparatus 104. The conduit 304 may comprise a skimmer (not shown in FIG. 3) that guides the analyte ions to the conduit 304, which in turn guides the analyte ions to the detector into the mass analyzer 102 and ultimately to the detector 103 (not shown in FIG. 3). Optionally, a gas conduit 309 may direct a drying gas 305 into the chamber 301 toward the droplets 221 in the chamber 301. The drying gas 305 is heated and assists further in desolvating droplets 221.

In a representative embodiment, the droplets 221 that emerge from the disruptor apparatus 104 are electrically charged. A voltage is established between the disruptor apparatus 104 and the conduit 304 so that the charged analyte ions are directed to the conduit 304 along trajectories 306. Most of the droplets 221 that are not provided to the conduit 304 continue to travel in the direction of the longitudinal axis 302 and are expelled at an exhaust port 308 along with gases 307.

As described above, providing droplets 221 of a smaller volume fosters more efficient separation of the mobile phase from the analytes. This is because the amount of time it takes for a droplet 221 to desolvate the mobile phase is directly related to the size of the drop: drops of lesser volume desolvate more rapidly than drops of greater volume. Faster desolvation time in turn means not only that a larger fraction of analyte ions are desolvated, but also means the distance that droplets 221 travel from outlet 211 until they are desolvated is shorter. In many known methods and apparatuses, many analyte ions are not ultimately provided to the mass analyzer 102, but rather are lost such as through an exhaust port 308. Often in known devices, the drops are lost before separation of the mobile phase and analytes occurs. By contrast, the droplets 221 are desolvated more rapidly and in a shorter distance, or in a smaller volume in the ion source 101 of FIG. 3. This facilitates more efficient transfer of analyte ions into the mass analyzer 102 by reducing space charge effects, which are the mutual electrostatic repulsion of ions as well as charged droplets 221.

Because disruptor apparatus 104 fragments the drops 220 (FIG. 2B) into droplets 221 of a comparatively small volume and the desolvation process occurs more rapidly. In certain embodiments, the droplets 221 may be provided directly to the conduit 304 and thus directly to the mass analyzer 102. In this manner, the disruptor apparatus 104 functions as an interface between the LC column and the mass spectrometer. Representative embodiments illustrating the use of the apparatus as such an interface are described presently in conjunction with FIG. 4.

Figure 4:
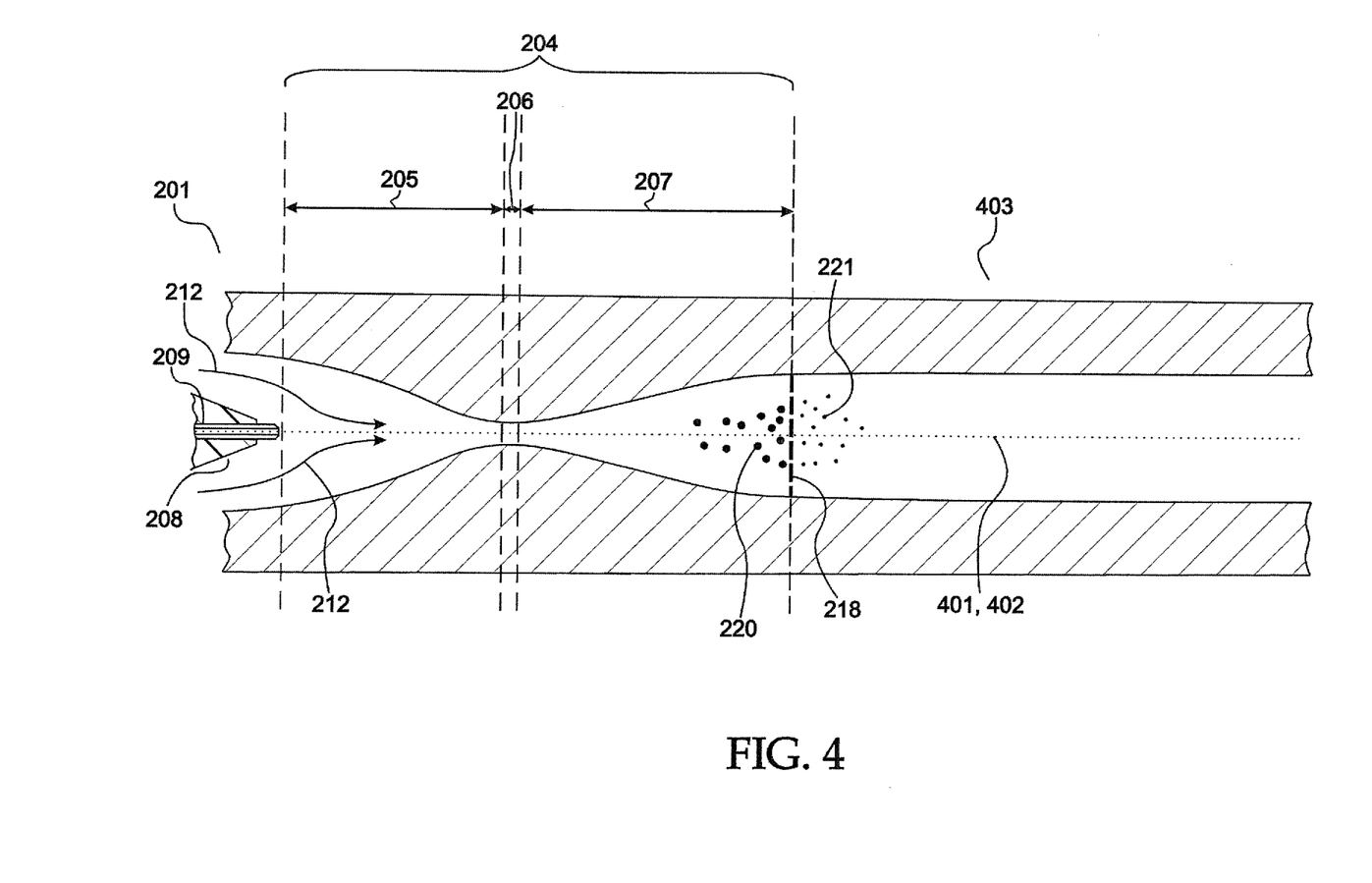
Figure 5:
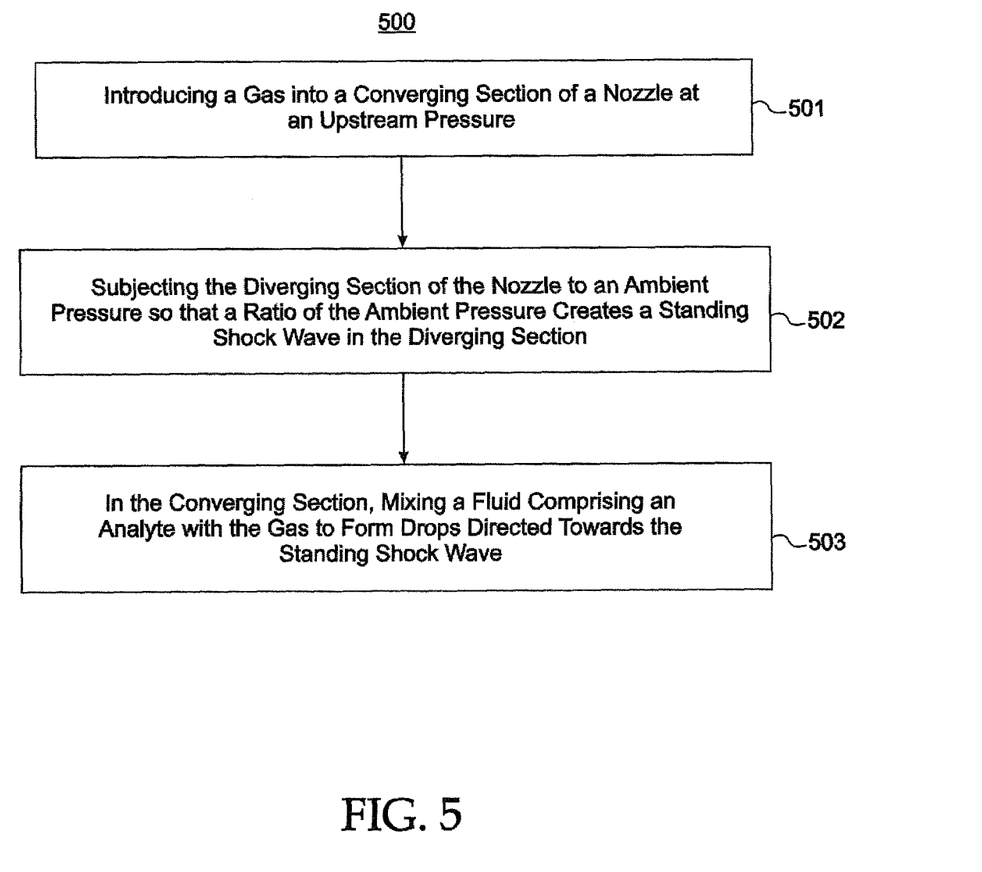

FIG. 4 shows cross-sectional views of the disruptor apparatus 104 provided to a conduit to a mass analyzer in accordance with representative embodiments. Many of the details provided in connection with the description of representative embodiments of FIGS. 1, 2A, 2B and 3 are germane to the presently described embodiments, and are not repeated in order to avoid obscuring the description of the embodiment of FIG. 4.

Specifically, FIG. 4 shows a cross-sectional view of a part of the first portion 201 of the disruptor apparatus 104 and a conduit 403 to a mass analyzer (not shown in FIG. 4) in accordance with a representative embodiment. Notably, the housing 300, the chamber 301, and similar components described in connection with representative embodiments in connection with FIG. 3 are not included in the presently described embodiment. Rather, the droplets 221 provided from the diverging section 207 of the nozzle 204, travel generally along a trajectory 401, and are provided directly to the conduit 304 to the mass analyzer. In this manner, the disruptor apparatus 104 functions as the ion source 101. As described in detail above, because the drops 220 have been fragmented into droplets 221 of comparatively small volumes, the time required for desolvation is reduced; and the distance that droplets 221 need to travel until the droplets 221 are desolvated is shorter. As such, the nozzle 204 of disruptor apparatus 104 may be provided directly to the conduit 304 to the mass analyzer 102.

In the present embodiment, the nozzle 204 and the conduit 403 share a common axis of symmetry 402, which is co-axial with the trajectory 401 of the droplets 221 passing from the nozzle 204 to the conduit 403. The nozzle 204 and the conduit 403 may be integral. Illustratively, the drops 220 from the outlet 211 traverse the throat 206 and are fragmented into droplets 221 by the standing shock wave 216 as described above. The droplets 221 are substantially completely desolvated, travel down the conduit 403 and are provided to the mass analyzer. Because of the comparatively short distance required for desolvation to occur, a greater portion of the analyte ions from the desolvated droplets 221 are provided to the conduit 403, and then to the mass analyzer through the comparatively direct connection of the nozzle to the conduit 403.

FIG. 5 shows a flow-chart of a method 500 in accordance with a representative embodiment. Many of the details provided in connection with the description of representative embodiments of FIGS. 1, 2A, 2B, 3 and 4 are germane to the presently-described embodiment, and are not repeated in order to avoid obscuring the description of the illustrative method.

At 501, the method comprises introducing a gas into the converging section of the nozzle at an upstream pressure. At 502, the method comprises subjecting the diverging section of the nozzle to an ambient pressure so that a ratio of the upstream pressure to the ambient pressure creates a standing shock wave in the diverging section. At 503, the method comprises mixing a fluid comprising an analyte with the gas to form drops directed towards the standing shock wave. The mixing is done in the converging section.

In view of this disclosure it is noted that the methods and devices can be implemented in keeping with the present teachings. Further, the various components, materials, structures and parameters are included by way of illustration and example only and not in any limiting sense. In view of this disclosure, the present teachings can be implemented in other applications and components, materials, structures and equipment to needed implement these applications can be determined, while remaining within the scope of the appended claims.

The invention claimed is:

1. In a disruptor apparatus comprising a nozzle, the nozzle comprising a throat, a converging section and a diverging section in tandem, a method comprising:

introducing a gas into the converging section of the nozzle at an upstream pressure;

subjecting the diverging section of the nozzle to an ambient pressure so that a ratio of the upstream pressure to the ambient pressure creates a standing shock wave in the diverging section; and subjecting drops of a fluid comprising an analyte to impact the standing shock wave, causing the drops to be broken into droplets having a smaller size than the drops, resulting in substantially complete desolvation of a mobile phase of a liquid chromatography (LC) fluid.

2. A method as claimed in claim 1, further comprising, before the subjecting, mixing a fluid comprising an analyte with the gas in the converging section to form the drops, and directing the drops towards the standing shock wave.

3. A method as claimed in claim 1, wherein the diverging section comprises an exit and the standing shock wave and the standing shock wave is located adjacent to the exit.

4. A method as claimed in claim 1, further comprising subjecting the converging section of the nozzle to an electric field.

5. A method as claimed in claim 1, wherein the inert gas attains a velocity in the diverging section at a speed of approximately Mach 2.0 or greater.

6. A method as claimed in claim 1, wherein the fragmenting substantially desolvates the droplets into ions and gas molecules.

7. A disruptor apparatus, comprising:

a nozzle comprising: a converging section; a diverging section; and a throat between the converging section and the diverging section;

a holder configured to receive a fluid conduit, which comprises an outlet located in the converging section, wherein the holder and the fluid conduit substantially share a common longitudinal axis; and a channel disposed about the holder and configured to guide a gas past the outlet of the fluid conduit, through the converging section, through the throat and into the diverging section where the gas travels at supersonic speed and establishes a standing shock wave in the diverging section.

8. A disruptor apparatus as claimed in claim 7, wherein the gas at least assists in nebulizing a fluid emerging from the outlet of the fluid conduit to form drops of a first size.

9. A disruptor apparatus as claimed in claim 8, wherein the standing shock wave is formed at or near an exit of the diverging section.

10. A disruptor apparatus as claimed in claim 9, wherein the drops are incident on the standing shock wave, and are fragmented by the shock wave into droplets of a second size that is smaller than the first size.

11. A disruptor apparatus as claimed in claim 7, wherein the nozzle and the fluid conduit are defined in an electrically-conducting material, and the holder is electrically insulating.

12. A mass spectrometer, comprising:
a disruptor apparatus, comprising:
a nozzle comprising: a converging section; a diverging section; and a throat between the converging section and the diverging section;
a holder configured to receive a fluid conduit, which comprises an outlet located in the converging section, wherein the holder and the fluid conduit substantially share a common longitudinal axis; and
a channel disposed about the holder and configured to guide a gas past the outlet of the fluid conduit, through the converging section, through the throat and into the diverging section where the gas travels at supersonic speed and establishes a standing shock wave in the diverging section.

13. A mass spectrometer as claimed in claim 12, wherein the gas at least assists in nebulizing a fluid emerging from the outlet of the fluid conduit to form drops of a first size.

14. A mass spectrometer as claimed in claim 12, wherein the standing shock wave is formed at or near an exit of the diverging section.

15. A mass spectrometer as claimed in claim 13, wherein the drops are incident on the standing shock wave, and are fragmented by the shock wave into droplets of a second size that is smaller than the first size.

16. A mass spectrometer as claimed in claim 13, wherein the nozzle and the fluid conduit are defined in electrically-conducting material, and the holder is electrically insulating.

17. A disruptor apparatus as claimed in claim 7, wherein the holder comprises orifices configured to direct the gas radially out of the holder and into the channel.

18. A mass spectrometer as claimed in claim 12, wherein the holder comprises orifices configured to direct the gas radially out of the holder and into the channel.

19. An ion source comprising the disruptor apparatus of claim 7.

* * * * *